(12) United States Patent
Horcajada et al.

(10) Patent No.: US 10,744,100 B2
(45) Date of Patent: Aug. 18, 2020

(54) COMPOSITIONS AND METHODS USING A POLYPHENOL FOR MUSCULOSKELETAL HEALTH

(71) Applicant: NESTEC S.A., Vevey (CH)

(72) Inventors: Marie Noelle Horcajada, Echenevex (FR); Fanny Membrez, Cugy (CH); Denis Breuille, Lausanne (CH); Claire Boutry, Corcelles pres Concise (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/180,754

(22) Filed: Nov. 5, 2018

(65) Prior Publication Data
US 2019/0070130 A1   Mar. 7, 2019

Related U.S. Application Data

(63) Continuation-in-part of application No. 15/776,451, filed as application No. PCT/EP2016/078014 on Nov. 17, 2016.

(60) Provisional application No. 62/256,401, filed on Nov. 17, 2015.

(51) Int. Cl.
| *A61K 31/12* | (2006.01) |
| *A61K 31/202* | (2006.01) |
| *A61P 21/00* | (2006.01) |
| *A61K 38/17* | (2006.01) |
| *A23L 33/105* | (2016.01) |
| *A23L 33/12* | (2016.01) |
| *A23L 33/19* | (2016.01) |

(52) U.S. Cl.
CPC ............ *A61K 31/12* (2013.01); *A23L 33/105* (2016.08); *A23L 33/12* (2016.08); *A23L 33/19* (2016.08); *A61K 31/202* (2013.01); *A61K 38/1709* (2013.01); *A61P 21/00* (2018.01); *A23V 2002/00* (2013.01)

(58) Field of Classification Search
CPC ....... A61P 21/00; A61K 31/202; A61K 31/12; A61K 38/17; A23L 33/12
See application file for complete search history.

(56) References Cited

U.S. PATENT DOCUMENTS

| 9,867,391 B2* | 1/2018 | Dardevet ............. A61K 31/198 |
| 2005/0153019 A1 | 7/2005 | Fuchs et al. |
| 2014/0249078 A1 | 9/2014 | Breuille et al. |
| 2014/0255511 A1* | 9/2014 | Dardevet ............. A61K 31/198 424/641 |
| 2015/0297536 A1 | 10/2015 | Deshpande et al. |
| 2016/0051814 A1* | 2/2016 | Arigoni ............. A61N 1/36003 604/20 |
| 2018/0353527 A1* | 12/2018 | Horcajada ............ A61K 31/202 |

FOREIGN PATENT DOCUMENTS

| WO | 2012097061 | 7/2012 | |
| WO | 2014161872 | 10/2014 | |
| WO | 2014170245 | 10/2014 | |
| WO | WO-2014170245 A1 * | 10/2014 | ......... A61N 1/36003 |
| WO | 2015094772 | 6/2015 | |
| WO | 2016058919 | 4/2016 | |

OTHER PUBLICATIONS

Nelson et al. J. Med. Chem. (2017), V.60, p. 1620-1637.*

* cited by examiner

Primary Examiner — Yong L Chu
(74) Attorney, Agent, or Firm — K&L Gates LLP

(57) ABSTRACT

A composition contains curcumin and can treat or prevent sarcopenia, reduce a loss of muscle functionality (e.g. muscle strength, gait speed, etc.), increase muscle functionality, and/or improve recovery of muscle functionality after muscle atrophy. The composition can be administered to an individual who is elderly and/or frail, optionally in a composition that further includes an omega-3 fatty acid and/or a protein source.

8 Claims, 16 Drawing Sheets

COMPOSITIONS AND METHODS USING A POLYPHENOL FOR MUSCULOSKELETAL HEALTH

CROSS REFERENCE TO RELATED APPLICATIONS

The present application is a continuation-in-part of U.S. Ser. No. 15/776,451 filed May 16, 2018, which is a National Stage of International Application No. PCT/EP2016/078014 filed Nov. 17, 2016, which claims priority to U.S. Provisional Patent Application No. 62/256,401 filed Nov. 17, 2015, the entire contents of which are incorporated herein by reference.

BACKGROUND

The present disclosure generally relates to compositions and methods which use one or more polyphenols to improve or maintain musculoskeletal health. More specifically, the present disclosure relates to administering a composition comprising one or more polyphenols to treat, prevent or reduce the progression of sarcopenia; reduce a loss of muscle functionality (e.g. muscle strength, gait speed, etc.); increase muscle functionality, and/or improve recovery of muscle functionality after muscle atrophy or injury.

Muscle loss manifests itself in several life-threating diseases, including sarcopenia. The balance between atrophy (loss) and hypertrophy (gain) is key to the maintenance of skeletal muscle mass. However, skeletal muscle is terminally differentiated, so an understanding of the mechanisms allowing this plasticity is central to long-term health and survival.

Sarcopenia is defined as the age-associated loss of muscle mass and functionality (including muscle strength and gait speed). Muscle functionality and physical ability decline with the loss of muscle mass. Impaired muscle functionality is highly predictive of the incidence of immobility, disability, and mortality in advanced age. With the rising elderly population, sarcopenia becomes increasingly prevalent such that 45% of the elderly U.S. population has moderate-to-severe symptoms. The U.S. health care direct and indirect costs attributable to sarcopenia reach nearly $19 billion. Therefore, prevention and/or treatment of sarcopenia would have a great impact on the health and quality of life of our society and consequently on the economy associated with health care. Unfortunately, the etiology and the physiopathological mechanism of sarcopenia are still poorly understood, making effective measures for prevention or treatment difficult.

One of the main hypotheses developed to explain the progressive muscle loss observed with aging is a decreased anabolic effect of meal ingestion due to a lower stimulation of muscle protein synthesis by the nutrients. This hypothesis is called muscle anabolic resistance. In addition, oxidative stress and/or low grade inflammation and/or mitochondrial dysfunction have also been demonstrated to be associated with frailty in the elderly and could be partly responsible for anabolic resistance either directly or through a decreased sensitivity of muscle to insulin.

SUMMARY

Without being bound by theory, the present inventors believe that muscle satellite cells and myoblasts may be central in the increase/loss of skeletal muscle mass and therefore may be involved in potential therapeutic interventions for muscle wasting diseases and ageing. The present disclosure aims to provide nutritional solutions to increase hypertrophy or decrease atrophy and thus limit the progression of sarcopenia during aging, to reduce a loss of muscle functionality, to increase muscle functionality, and/or to improve recovery of muscle functionality after muscle atrophy.

Polyphenols have potent antioxidant and/or anti-inflammatory properties and are present in many plant materials such as cocoa, teas, and fruits such as berries. Nevertheless, to the best knowledge of the present inventors, nothing is known or has been published regarding an impact of polyphenols such as curcumin, oleuropein or rutin on triggering muscle hypertrophy or limiting atrophy and thus impacting overall muscle mass (maintenance or limitation of loss).

Accordingly, in a general embodiment, the present disclosure provides a method of reducing a loss of muscle functionality in an individual, increasing muscle functionality in an individual, and/or improving recovery of muscle functionality after muscle atrophy in an individual. It also helps to limit or avoid anabolic resistance. The method comprises administering a composition comprising a polyphenol to the individual.

In an embodiment, the polyphenol is selected from the group consisting of oleuropein, rutin, quercetin, curcumin and combinations thereof.

In an embodiment, the composition further comprises a fatty acid. The fatty acid can be an n-3 fatty acid.

In an embodiment, the composition further comprises a protein source. The protein source can comprise a protein source from animal or plant origin, for example milk proteins, soy proteins, and/or pea proteins and combinations thereof. In a preferred embodiment, the protein source is selected from the group consisting of whey protein; casein protein; pea protein; soy protein; wheat protein; corn protein; rice protein; proteins from legumes, cereals and grains; and combinations thereof. Additionally or alternatively, the protein source may comprise a protein from nuts and/or seeds.

In an embodiment, the composition comprises a protein source, rutin and an n-3 fatty acid.

In another embodiment, the composition comprises a protein source, curcumin and an n-3 fatty acid.

In an embodiment, the muscle functionality comprises a characteristic selected from the group consisting of muscle strength, gait speed, and combinations thereof.

In an embodiment, the individual has sarcopenia.

In another embodiment, the individual is an elderly having mobility issues or muscle weakness.

In another embodiment, the present disclosure provides a composition comprising a polyphenol in a nutritional amount that is therapeutically effective for at least one of: (i) treating sarcopenia in an individual having sarcopenia, (ii) preventing sarcopenia in an individual, (iii) reducing a loss of muscle functionality in an individual, (iv) increasing muscle functionality in an individual, or (v) improving recovery of muscle functionality after muscle atrophy in an individual.

In an embodiment, the polyphenol is selected from the group consisting of oleuropein, rutin, quercetin, curcumin and combinations thereof.

In an embodiment, the composition is selected from the group consisting of food compositions, dietary supplements, nutritional compositions, nutraceuticals, powdered nutritional products to be reconstituted in water or milk before consumption, food additives, medicaments, drinks, and combinations thereof.

In another embodiment, the present disclosure provides a method of preventing sarcopenia in an individual. The method comprises administering a composition comprising a polyphenol to an individual at risk thereof.

In an embodiment, the polyphenol is selected from the group consisting of oleuropein, rutin, quercetin, curcumin and combinations thereof.

In another embodiment, the present disclosure provides a method of making a food composition. The method comprises adding a polyphenol to another ingredient to form the food composition, the polyphenol added in an amount therapeutically effective to reduce a loss of muscle functionality in an individual, increase muscle functionality in an individual, and/or improve recovery of muscle functionality after muscle atrophy in an individual.

An advantage of the present disclosure is to provide a composition, such as a food product or a food supplement, that treats sarcopenia in individuals.

Another advantage of the present disclosure is to provide a composition, such as a food product or a food supplement, that prevents sarcopenia.

Still another advantage of the present disclosure is to provide a composition, such as a food product or a food supplement, that reduces a loss of muscle functionality (e.g. muscle strength, gait speed, etc.) in individuals, relative to the loss that would be experienced during consumption of a diet lacking the composition.

An additional advantage of the present disclosure is to provide a composition, such as a food product or a food supplement, that increases muscle functionality (e.g. muscle strength, gait speed, etc.) in individuals, relative to the muscle functionality (e.g. muscle strength, gait speed, etc.) that would be present from consumption of a diet lacking the composition.

Another advantage of the present disclosure is to provide a composition, such as a food product or a food supplement, that improves recovery of muscle functionality (e.g. muscle strength, gait speed, etc.) after muscle atrophy in individuals, relative to the recovery that would be present from consumption of a diet lacking the composition.

Yet another advantage of the present disclosure is to beneficially promote reduction, prevention, or treatment of sarcopenia in individuals.

Another advantage of the present disclosure is to provide nutritional strategies to reduce development of sarcopenia in individuals, especially to reduce loss of muscle functionality (e.g. muscle strength, gait speed, etc.) in elderly humans.

Additional features and advantages are described in, and will be apparent from, the following Detailed Description and the Figures.

BRIEF DESCRIPTION OF DRAWINGS

FIG. 1: Effect of oleuropein (OLP) at 1.01M on creatine kinase activity (CK). Murine myoblasts (C2C12) were culture in monolayer during 4 days with or without oleuropein. Data were normalized to protein content and results were expressed as mean±S.E.M.

FIG. 2: Effect of oleuropein (OLP) at 1.5 μM on MyoD expression. Murine myoblasts (C2C12) were culture in monolayer during 4 days with or without oleuropein. Data were normalized to GAPDH (Glyceraldehyde 3-phosphate dehydrogenase) mRNA levels and results were expressed as mean±S.E.M.

FIG. 3: Effect of oleuropein (OLP) at 1.5 μM on Myogenin (MyoG) expression. Murine myoblasts (C2C12) were culture in monolayer during 4 days with or without oleuropein. Data were normalized to GAPDH (Glyceraldehyde 3-phosphate dehydrogenase) mRNA levels and results were expressed as mean f S.E.M.

FIG. 4: Effect of oleuropein (OLP) at 1.5 μM on chemokine (C—X—C motif) ligand 1 (CXCL-1) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M.

FIG. 5: Effect of oleuropein (OLP) at 1.5 μM on Chemokine (C—C motif) ligand 5 (CCL-5) expression also known as RANTES (regulated on activation, normal T cell expressed and secreted). Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M.

FIG. 6: Effect of oleuropein (OLP) at 1.5 μM on A disintegrin and metalloproteinase with thrombospondin motifs 4 (ADAMTS-4) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean f S.E.M.

FIG. 7: Effect of oleuropein (OLP) at 1.5 μM on NF-κB (nuclear factor kappa-light-chain-enhancer of activated B cells) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean f S.E.M.

FIG. 8: Effect of oleuropein (OLP) at 1.5 μM on Prostaglandin-endoperoxide synthase 2 also known as cyclooxygenase-2 (COX-2) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean f S.E.M.

FIG. 9: Effect of oleuropein (OLP) at 1.5 μM on Interleukin-6 (IL-6) expression. Murine myoblasts (C2C12) were culture in monolayer during 4 days with or without oleuropein in presence or in absence of TNF-α stimulation (10 ng/ml). Data were 5 normalized to GAPDH (Glyceraldehyde 3-phosphate dehydrogenase) mRNA levels and results were expressed as mean±S.E.M.

FIG. 10: Effect of oleuropein (OLP) at 1.5 μM on Forkhead box O3 (FOXO3) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M.

FIG. 11: Effect of rutin and n-3 fatty acids (RUT+n-3 FA) on lean gain in old rats. 20 months-old rats were fed either a control diet or the same diet supplemented with rutin and n-3 FA for 3 months. Results were expressed as mean±S.E.M.

FIG. 12: Effect of rutin and n-3 fatty acids (RUT+n-3 FA) on evolution of gait speed from baseline to 3 months supplementation in old rats. 20 months-old rats were fed either a control diet or the same diet supplemented with rutin and n-3 FA for 3 months. Results were expressed as mean±S.E.M.

FIG. 13: Effect of rutin and n-3 fatty acids (RUT+n-3 FA) on low grade inflammation (alpha 2 macroglobulin) in old rats. 20 months-old rats were fed either a control diet or the same diet supplemented with rutin and n-3 FA for 3 months. Results were expressed as mean±S.E.M.

FIG. 14: Effects of curcumin (CUR), rutin (RUT), n-3 fatty acid (n-3 FA) and the combination of either curcumin and n-3 FA (CUR+n-3 FA) or rutin and n-3 FA (RUT+n-3 FA) on evolution of gait speed from baseline to 3 months supplementation in old rats. 20 months-old rats were fed either a control diet or the diet supplemented with rutin or curcumin and optionally n-3 FA for 3 months. Results were expressed as mean±S.E.M.

FIG. 15: Effect of curcumin (CUR), rutin (RUT), n-3 fatty acid (n-3 FA) and the combination of either curcumin and n-3 FA (CUR+n-3 FA) or rutin and n-3 FA (RUT+n-3 FA) on MFN2/DRP1 protein level ratio in old rats. 20 months-old rats were fed either a control diet or the diet supplemented with rutin or curcumin and optionally n-3 FA. Results were expressed as mean±S.E.M.

DETAILED DESCRIPTION

Figure 1:
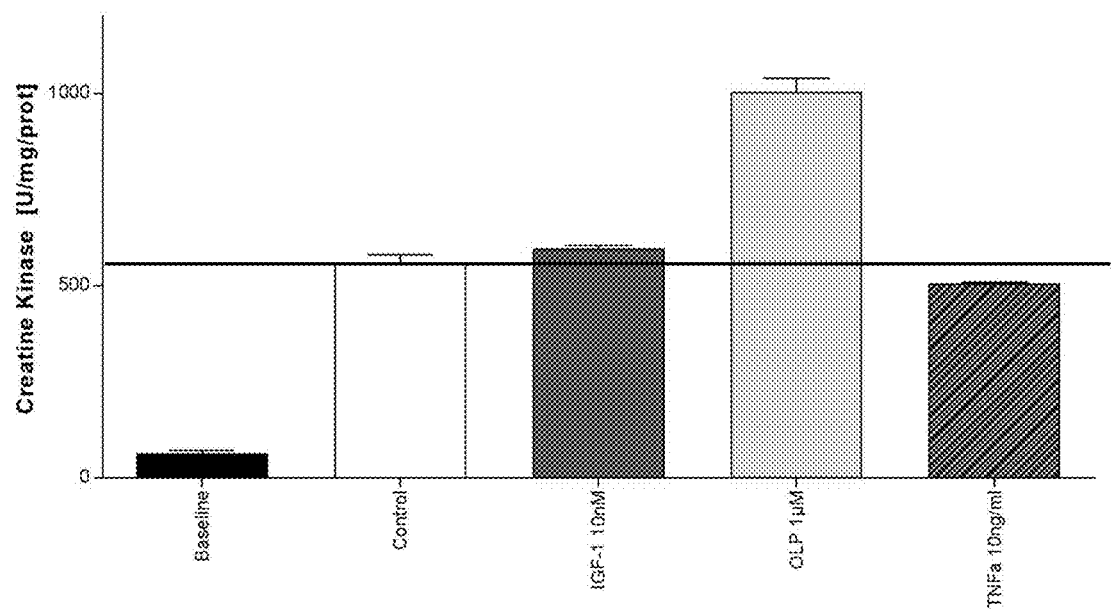
FIGS. 1-15 show data from the experimental trial disclosed herein.

All percentages are by weight of the total weight of the composition unless expressed otherwise. Similarly, all ratios are by weight unless expressed otherwise. When reference is made to the pH, values correspond to pH measured at 25° C. with standard equipment. As used herein, "about," "approximately" and "substantially" are understood to refer to numbers in a range of numerals, for example the range of –10% to +10% of the referenced number, preferably –5% to +5% of the referenced number, more preferably –1% to +1% of the referenced number, most preferably –0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used herein and in the appended claims, the singular form of a word includes the plural, unless the context clearly dictates otherwise. Thus, the references "a," "an" and "the" are generally inclusive of the plurals of the respective terms. For example, reference to "an ingredient" or "a method" includes a plurality of such "ingredients" or "methods." The term "and/or" used in the context of "X and/or Y" should be interpreted as "X," or "Y," or "X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components. Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

The term "elderly" means a person above the age of 60 years, preferably above 63 years, and more preferably above 65 years. The term "frail" refers to a person which is physically weak, i.e. not strong, but fragile.

The terms "treatment" and "treating" include any effect that results in the improvement of the condition or disorder, for example lessening, reducing, modulating, or eliminating the condition or disorder. The term does not necessarily imply that a subject is treated until total recovery. Non-limiting examples of "treating" or "treatment of" a condition or disorder include: (1) inhibiting the condition or disorder, i.e. arresting the development of the condition or disorder or its clinical symptoms and (2) relieving the condition or disorder, i.e. causing the temporary or permanent regression of the condition or disorder or its clinical symptoms. A treatment can be patient- or doctor-related.

The terms "prevention" or "preventing" mean causing the clinical symptoms of the referenced condition or disorder to not develop in an individual that may be exposed or predisposed to the condition or disorder but does not yet experience or display symptoms of the condition or disorder. The terms "condition" and "disorder" mean any disease, condition, symptom, or indication.

The relative terms "improved," "increased," "enhanced" and the like refer to the effects of the composition comprising one or more polyphenols (disclosed herein) relative to a composition lacking polyphenols but otherwise identical.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the essential elements and limitations described herein, as well as any additional or optional ingredients, components, or limitations described herein or otherwise useful in a diet.

As used herein, "complete nutrition" contains sufficient types and levels of macronutrients (protein, fats and carbohydrates) and micronutrients to be sufficient to be a sole source of nutrition for the animal to which the composition is administered. Individuals can receive 100% of their nutritional requirements from such complete nutritional compositions.

A "polyphenol" is a compound comprising an aromatic ring bearing one or more hydroxy substituents, including functional derivatives. Antioxidant agents containing polyphenols include plant, algal or fungal extracts or fractions rich in polyphenols, including flavonoids (isoflavones, anthocyanins, proanthocyanidins and anthocyanidins, flavans, flavonols, flavones and flavanones). Specific examples of bioflavonoids are catechins (catechin, epicatechin, gallocatechin, epigallocatechin, epicatechin gallate, epigallocatechin gallate), oleuropein, quercetin, rutin, hesperidin, curcumin and genistein.

The term "unit dosage form," as used herein, refers to physically discrete units suitable as unitary dosages for human and animal subjects, each unit containing a predetermined quantity of the composition disclosed herein in an amount sufficient to produce the desired effect, preferably in association with a pharmaceutically acceptable diluent, carrier or vehicle. The specifications for the unit dosage form depend on the particular compounds employed, the effect to be achieved, and the pharmacodynamics associated with each compound in the host. In some embodiments, the unit dosage form can be a predetermined amount of the active compounds in a serving of a food product, a predetermined amount of powder in a sachet, a predetermined amount of the active compounds in a capsule or a tablet, or a predetermined amount of the active compounds in a predetermined volume of liquid, preferably a therapeutically or prophylactically effective amount or a predetermined portion of a therapeutically or prophylactically effective amount.

An aspect of the present disclosure is a composition comprising one or more polyphenols for treatment or prevention of sarcopenia, for reducing a loss of muscle functionality (e.g. muscle strength, gait speed, etc.), for increasing muscle functionality (e.g. muscle strength, gait speed, etc.), and/or for improving recovery of muscle functionality (e.g. muscle strength, gait speed, etc.) after muscle atrophy in an individual such as a mammal, e.g., a human. Another aspect of the present disclosure is a method comprising administering a therapeutically effective amount of a composition comprising one or more polyphenols to an individual to treat the individual for sarcopenia, prevent sarcopenia in the individual, reduce a loss of muscle functionality (e.g. muscle strength, gait speed, etc.) in the individual, increase the muscle functionality (e.g. muscle strength, gait speed, etc.) in the individual, and/or improve recovery of muscle functionality (e.g. muscle strength, gait speed, etc.) after muscle atrophy in the individual. In an embodiment, the composition comprises the one or more polyphenols in a total concentration of about 1 µM.

Muscle atrophy, as treated or prevented according to the present disclosure, may be caused by many reasons. For example, it may result from lack of physical activity, such as from immobilization or low physical activity associated with aging (sarcopenia associated with aging process), hip-fracture recovery, or several co-morbidities of diseases, such as cancer, AIDS, congestive heart failure, COPD (chronic obstructive pulmonary disease), renal failure, trauma, sepsis, and severe burns, for example. Muscle atrophy may also result from insufficient or inappropriate nutrition or starvation. Very commonly, muscle atrophy results from disuse or insufficient use of the respective muscle.

The muscle referenced in the present disclosure is preferably a skeletal muscle. For example, the composition disclosed herein may be used to reduce the loss of muscle functionality in the arms and/or the legs of the individual. The muscle may be one or more of the following: gastrocnemius, tibialis, soleus, extensor, digitorum longus (EDL), biceps femoris, semitendinosus, semimembranosus, or gluteus maximus.

Muscle atrophy may result in the disorder of sarcopenia, i.e. lost muscle mass, size, and functionality because of aging. The muscle atrophy may be of different grades, such as severe muscle atrophy as in extreme frailty of elderly persons. Extremely frail elderly persons can have difficulty in every-day activities and taking care of themselves. Muscle atrophy of a less severe degree will allow some movement and some muscle activity, but the muscle activity is insufficient to sustain the complete muscle tissue. The mechanisms involved in treating or preventing age-associated sarcopenia are different from treating or preventing loss of muscle function in younger persons.

The composition disclosed herein comprises one or more polyphenols and can reduce loss of muscle functionality and/or improve muscle functionality in an individual who is administered the composition, relative to a diet lacking such a composition. In a preferred embodiment, the one or more polyphenols are food-grade polyphenols. A compound is considered "food-grade" if it is generally accepted and considered safe for food applications.

Mixtures of polyphenols may be used, such as two or more polyphenols. Polyphenols may also be provided as food compositions rich in polyphenols or extracts thereof. Plant extracts rich in or enriched in polyphenols are particularly suitable for the present invention.

Cocoa, coffee and tea are high in polyphenols. Fruit extracts or dried fruits may be used as a source of polyphenols, for example pears, apples, grapes, cranberries, blueberries, blackberries, raspberries, strawberries, blackcurrants, cherries, plums, and/or pomegranates. Also some nuts and seeds are rich in polyphenols, such as chestnuts, hazel nuts and flaxseed. Non-limiting examples of vegetables high in polyphenols are cabbage, broccoli, beetroot, artichoke heads, black olives, black beans, celery, onions, parsley and spinach.

The one or more polyphenols may be a purified compound or a partially purified compound. Non-limiting examples of suitable polyphenols are phenolic acids; flavonoids, such as flavonols, flavones, isoflavones, flavanones, anthocyanins, and flavanols; stilbenes; and lignans. In an embodiment, the one or more polyphenols comprise a flavonol and/or a flavonol glycoside. As a non-limiting example, the one or more polyphenols can comprise one or more of oleuropein, rutin, curcumin or quercetin.

The one or more polyphenols may each be present in amount of from 0.01 mg to about 1 g, preferably from 0.1 mg to 1 g, even more preferably from 1 mg to about 1 g per serving.

The effective amount of a composition according to the present invention which is required to achieve a therapeutical effect will, of course, vary with the particular composition, the route of administration, the age and condition of the recipient, and the particular disorder or disease being treated.

As an illustration, a RTD (ready to drink) will contain from 0.01 mg to 500 mg of each active ingredient per serving, more preferably about 250 mg per serving.

In addition to the one or more polyphenols, the composition can further comprise a protein source from animal or plant origin, for example milk proteins, soy proteins, and/or pea proteins. In a preferred embodiment, the protein source is selected from the group consisting of whey protein; casein protein; pea protein; soy protein; wheat protein; corn protein; rice protein; proteins from legumes, cereals and grains; and combinations thereof. Additionally or alternatively, the protein source may comprise a protein from nuts and/or seeds.

The protein source may comprise whey protein. The whey protein may be unhydrolyzed or hydrolyzed whey protein. The whey protein may be any whey protein, for example the whey protein can be selected from the group consisting of whey protein concentrates, whey protein isolates, whey protein micelles, whey protein hydrolysates, acid whey, sweet whey, modified sweet whey (sweet whey from which the caseino-glycomacropeptide has been removed), a fraction of whey protein, and any combination thereof. In a preferred embodiment, the whey protein comprises whey protein isolate and/or modified sweet whey.

As noted above, the protein source can be from animal or plant origin, for example milk proteins, soy proteins, and/or pea proteins. In an embodiment, the protein source comprises casein. Casein may be obtained from any mammal but is preferably obtained from cow milk and preferably as micellar casein.

In an embodiment of the invention the composition comprises protein in an amount such that the intake of protein, preferably whey, is 5-50 g protein per day, such as from 12-40 g protein per day, preferably from 15-30 g protein per day, such as from 16-25 g protein per day, even more preferably 20 g protein per day.

The composition can comprise one or more branched chain amino acids. For example, the composition can comprise leucine, isoleucine and/or valine. The protein source in the composition may comprise leucine in free form and/or leucine bound as peptides and/or proteins such as dairy, animal or vegetable proteins. In an embodiment, the composition comprises the leucine in an amount up to 10 wt % of the dry matter of the composition. Leucine can be present as D- or L-leucine and preferably the L-form. If the composition comprises leucine, the composition can be administered in a daily dose that provides 0.01 to 0.04 g of the leucine per kg body weight, preferably 0.02 to 0.035 g of the leucine per kg body weight. Such doses are particularly applicable to complete nutrition compositions, but one of ordinary skill will readily recognize how to adapt these doses for an oral nutritional supplement (ONS).

In an embodiment, the composition comprising one or more polyphenols further comprises a fatty acid. The fatty acid may be any fatty acid and may be one or more fatty acids, such as a combination of fatty acids. The fatty acid preferably comprises an essential fatty acid, such as the essential polyunsaturated fatty acids, namely linoleic acid (C18:2n-3) and α-linolenic acid (C18:3n-3). The fatty acid may comprise long-chain polyunsaturated fatty acids, such as eicosapentaenoic acid (C20:5n-3), arachidonic acid (C20:4n-6), docosahexaenoic acid (C22:6n-3), or any combination thereof. In a preferred embodiment, the fatty acid comprises an n-3 (omega 3) fatty acid and/or an n-6 (omega 6) fatty acid. The fatty acid preferably comprises eicosapentaenoic acid.

The fatty acid may be derived from any suitable source containing fatty acids, such as coconut oil, rapeseed oil, soya oils, corn oil, safflower oil, palm oil, sunflower oil or egg yolk. The source of the fatty acid is preferably fish oil.

The n-3 fatty acid according to the present invention is usually at least 10 wt %, preferably at least 15 wt %, based on total lipid content. In a preferred embodiment the daily amount is from 500 mg to 5 g, preferably 500 mg to 2.5 g, more preferably 1.5 g to 2 g n-3 fatty acid per day.

In addition to the one or more polyphenols, another anti-inflammatory compounds or antioxidant may be used in the composition. For example, the additional antioxidants may be provided as food compositions that are rich in antioxidants or as extracts thereof. A food composition that is "rich in antioxidants" has an ORAC (oxygen radical absorbance capacity) rating of at least 100 per 100 g of the composition.

In a most preferred embodiment, the composition comprises at least a protein source, rutin and an n-3 fatty acid. In another most preferred embodiment, the composition comprises at least a protein source, curcumin and an n-3 fatty acid. The protein source preferably comprises whey.

In another preferred embodiment, the composition comprises at least a protein source, curcumin and an n-3 fatty acid. The protein source preferably comprises whey. In a more preferred embodiment, this composition is administered to provide a daily amount about 20 g whey; 500 mg polyphenols (e.g. curcumin or rutin); 1500 mg n-3 fatty acid.

In an embodiment, the composition further comprises vitamin D. Compositions according to the invention may for example comprise Vitamin D in an amount of from 800 to 1200 IU per serving.

The composition comprising one or more polyphenols can be administered to an individual such as a human, e.g., an elderly human, in a therapeutically effective dose. The therapeutically effective dose can be determined by the person skilled in the art and will depend on a number of factors known to those of skill in the art, such as the severity of the condition and the weight and general state of the individual.

The composition may be administered to an individual in an amount sufficient to prevent or at least partially reduce the risk of developing sarcopenia in instances where the condition of sarcopenia has yet not been developed in the individual. Such an amount is defined to be "a prophylactically effective dose." Again, the precise amounts depend on a number of factors relating to the individual, such as their weight, health and how much muscle functionality (e.g. muscle strength, gait speed, etc.) is being lost.

The composition is preferably administered as a supplement to the diet of an individual daily or at least twice a week. In an embodiment, the composition is administered to the individual consecutively for a number of days, preferably until an increase in muscle functionality (e.g. muscle strength, gait speed, etc.) relative to that before administration is achieved. For example, the composition can be administered to the individual daily for at least 30, 60 or 90 consecutive days. As another example, the composition can be administered to the individual for a longer period, such as a period of 1, 2, 3, 4, 5, 6, 7, 8, 9 or 10 years.

In a preferred embodiment, the composition is administered to the individual for at least 3 months, for example a period of 3 months to 1 year, and preferably for at least 6 months.

The above examples of administration do not require continuous daily administration with no interruptions. Instead, there may be some short breaks in the administration, such as a break of two to four days during the period of administration. The ideal duration of the administration of the composition can be determined by those of skill in the art.

In a preferred embodiment, the composition is administered to the individual orally or enterally (e.g. tube feeding).

For example, the composition can be administered to the individual as a beverage, a capsule, a tablet, a powder or a suspension.

The composition can be any kind of composition that is suitable for human and/or animal consumption. For example, the composition may be selected from the group consisting of food compositions, dietary supplements, nutritional compositions, nutraceuticals, powdered nutritional products to be reconstituted in water or milk before consumption, food additives, medicaments, beverages and drinks. In an embodiment, the composition is an oral nutritional supplement (ONS), a complete nutritional formula, a pharmaceutical, a medical or a food product. In a preferred embodiment, the composition is administered to the individual as a beverage. The composition may be stored in a sachet as a powder and then suspended in a liquid such as water for use.

In some instances where oral or enteral administration is not possible or not advised, the composition may also be administered parenterally.

In some embodiments, the composition is administered to the individual in a single dosage form, i.e. all compounds are present in one product to be given to an individual in combination with a meal. In other embodiments, the composition is co-administered in separate dosage forms, for example the one or more polyphenols separately from one or more of the other components of the composition, and/or or a portion of the one or more polyphenols separately from another portion of the one or more polyphenols.

The present disclosure also provides a kit comprising curcumin and an omega-3 fatty acid in one or more containers. In some embodiments, one or more of these compounds can be isolated compounds.

In an embodiment of the kit, the curcumin and the omega-3 fatty acid can be provided together in one or more prepackaged unit dosage forms, for example in separate containers that each contain a dried powder such that each container contains one prepackaged unit dosage form.

In another embodiment, the kit can comprise a plurality of compositions for admixing together to form one or more of the compositions disclosed herein. For example, the kit can contain two or more dried powders in separate containers relative to each other, the separate powders each containing a portion of the final unit dosage form. As a non-limiting example of such an embodiment, the kit can contain one or more first containers that house the curcumin and can also contain one or more second containers that house the omega-3 fatty acid. The content of one of the first containers can be admixed with one of the second containers to form at least a portion of the unit dosage form of the composition.

EXAMPLE

The following non-limiting example presents scientific data developing and supporting the concept of administering a composition comprising one or more polyphenols to treat sarcopenia, prevent sarcopenia, reduce a loss of muscle functionality (e.g. muscle strength, gait speed, etc.), increase the muscle functionality (e.g. muscle strength, gait speed, etc.), and/or improve recovery of muscle functionality (e.g. muscle strength, gait speed, etc.) in an individual to whom the composition is administered.

Murine C2C12 myoblastic cell line (satellite cells from thigh muscle) is a good representation of muscle atrophy and hypertrophy. C2C12 cells differentiate in multinucleated myotubes. Myoblast differentiation and then myotube formation is biochemically observed by measuring the creatine kinase (CK) activity in the C2C12 cells.

Exp. 1: In the model used by the present inventors, C2C12 cells were treated with two polyphenols: oleuropein (from olive leaves) and quercetin (aglycone form of rutin). Tumor necrosis factor-alpha (TNF-α), which is a pleiotropic cytokine implicated as a mediator of muscle wasting in many states and ageing, was used as control of muscle atrophy. Polyphenol treatments were done in presence or in absence of TNF-a. Moreover, insulin-like growth factor-1 (IGF-1) was used as control of hypertrophy (FIG. 1).

The results showed that at 1 μM, oleuropein was able to increase myotube differentiation (hypertrophy).

Exp. 2: In the model used by the present inventors, C2C12 myoblasts were treated with oleuropein (1.5 μM), in presence or absence of TNF-a (10 ng/ml), for 4 days. TNF-α (Tumor necrosis factor-alpha) is a pleiotropic cytokine implicated as a mediator of muscle wasting in many states and ageing, and was used as control of muscle atrophy. TNF-α was also used to induce inflammatory conditions for C2C12. At day 3 and 4, markers of myotubes differentiation, myogenin D (MyoD) (FIG. 2) and MyoG (FIG. 3), were increased by oleuropein in non inflammatory conditions, suggesting a stimulation of muscle hypertrophy. In inflammatory conditions (with TNF-a), expression of specific muscle inflammatory cytokines, C—X—C motif ligand 1 (CXCL-1) (FIG. 4) and C—C motif ligand 5 (CCL-5) (FIG. 5), were decreased by oleuropein at day 4, suggesting a decrease of inflammatory response of muscle cells. Other inflammatory cytokines, non muscle specific were decreased (nuclear factor kappa-light-chain-enhancer of activated B cells—NFK-B (FIG. 7), cyclooxygenase-2—Cox-2 (FIG. 8) and interleukin-6—IL-6 (FIG. 9) showing the anti-inflammatory properties of oleuropein. Finally, A disintegrin and metalloproteinase with thrombospondin motifs 4 (AD-AMTS-4) (FIG. 6) was also decreased by oleuropein. Muscle protein breakdown was evaluated in our model by measuring Forkhead box 03 (FOXO3) (FIG. 10), and was decreased by oleuropein at day 3 and 4.

FIG. 1 shows the effect of oleuropein (OLP) at 1.0 μM on creatine kinase activity (CK). Murine myoblasts (C2C12) were culture in monolayer during 4 days with or without oleuropein. Data were normalized to protein content and results were expressed as mean f S.E.M. Baseline: basal control of non-differentiated cells fed with differentiated in growth medium. Control: basal control with differentiated medium (DM) (2% Horse serum, 1% Penicillin Streptomycin, DMEM high glucose). TNFa 10 ng/ml: tumor necrosis factor alpha at a concentration of 10 ng/ml in DM (control of atrophy). IGF-1 10 nM: Insulin-like growth factor 1 at a concentration of 10 nM in DM (control of hypertrophy). OLP 1 μM: Oleuropein at a concentration of 1.0 μM in DM.

Figure 2:
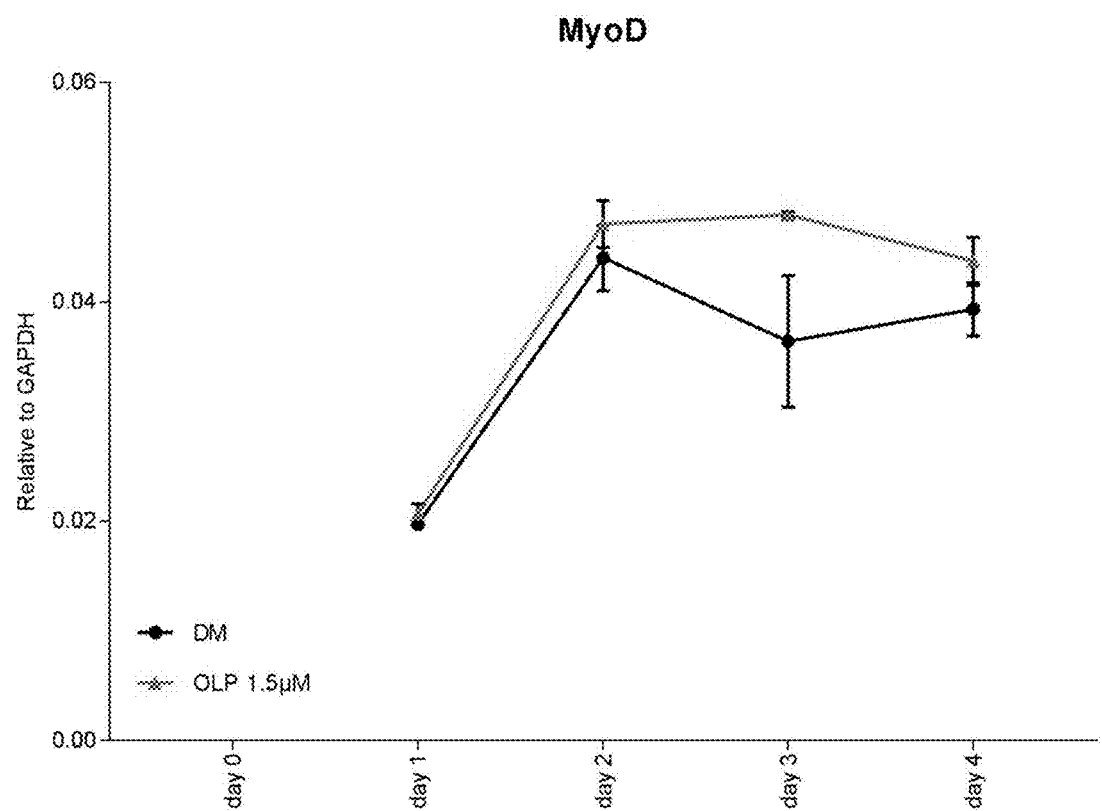

FIG. 2 shows the effect of oleuropein (OLP) at 1.5 μM on MyoD expression. Murine myoblasts (C2C12) were culture in monolayer during 4 days with or without oleuropein. Data were normalized to GAPDH (Glyceraldehyde 3-phosphate dehydrogenase) mRNA levels and results were expressed as mean f S.E.M. DM: basal control with differentiated medium (2% Horse serum, 1% Penicillin Streptomycin, DMEM high glucose). OLP 1.5 μM: Oleuropein at a concentration of 1.5 μM in DM.

Figure 3:
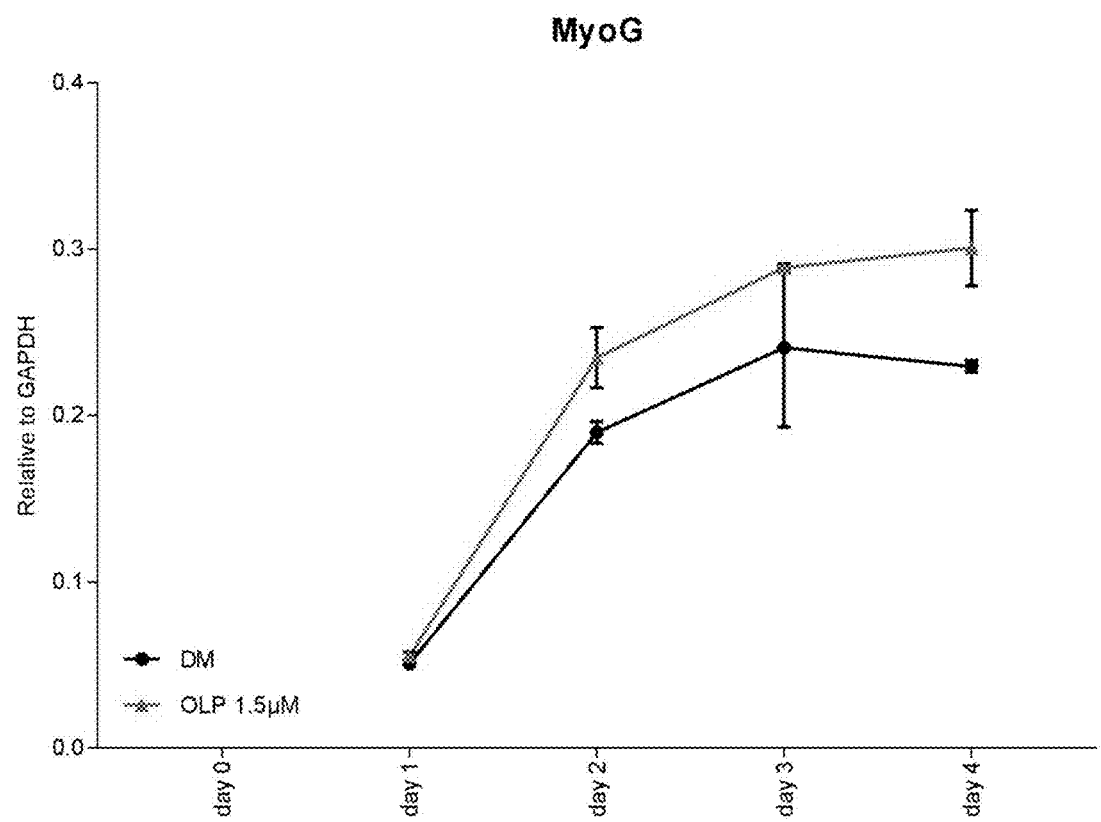

FIG. 3 shows the effect of oleuropein (OLP) at 1.5 μM on Myogenin (MyoG) expression. Murine myoblasts (C2C12) were culture in monolayer during 4 days with or without oleuropein. Data were normalized to GAPDH (Glyceraldehyde 3-phosphate dehydrogenase) mRNA levels and results were expressed as mean f S.E.M. DM: basal control with differentiated medium (2% Horse serum, 1% Penicillin Streptomycin, DMEM high glucose). OLP 1.5 μM: Oleuropein at a concentration of 1.5 μM in DM.

Figure 4:
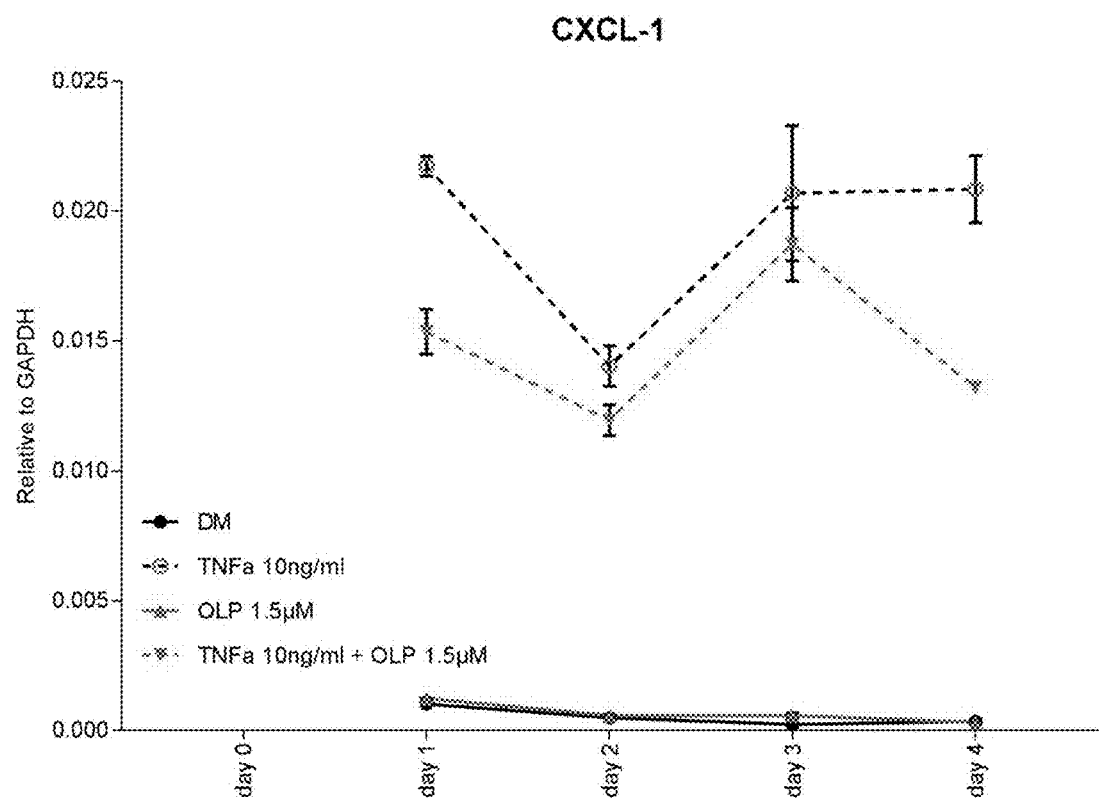
Figure 5:
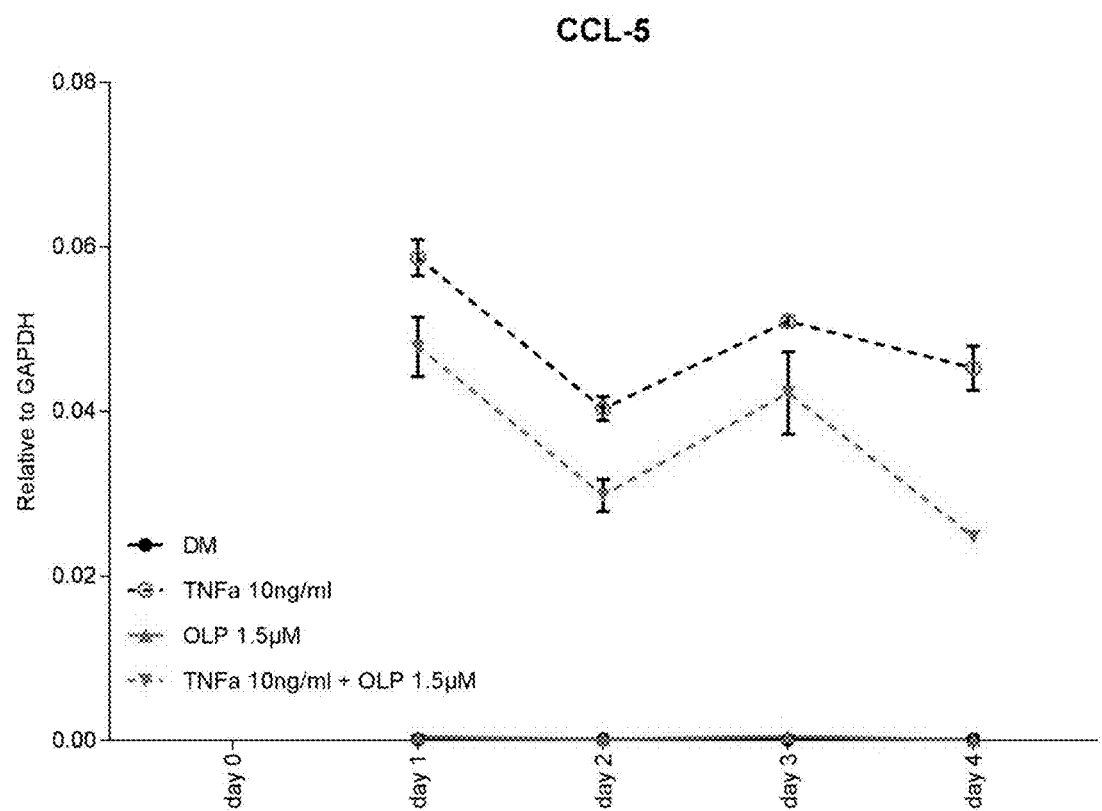
Figure 6:
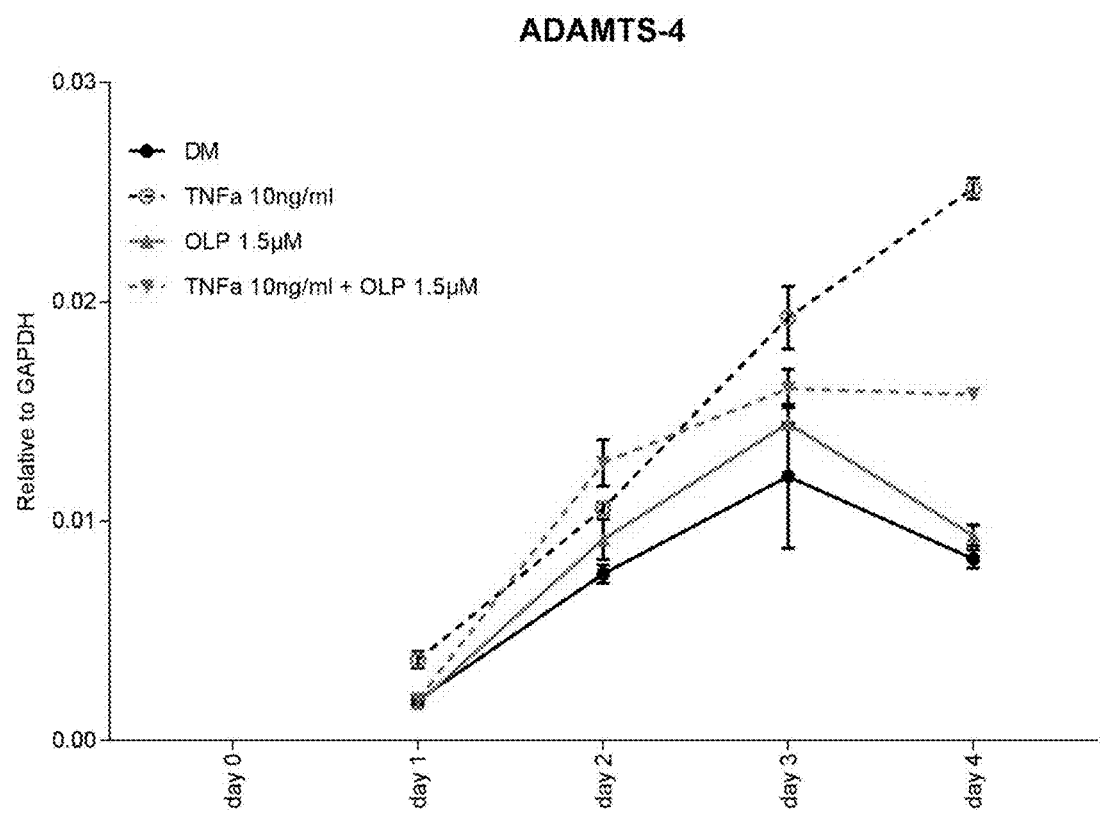

FIG. 4 shows the effect of oleuropein (OLP) at 1.5 μM on chemokine (C—X—C motif) ligand 1 (CXCL-1) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogensse) mRNA levels and results were expressed as mean f S.E.M. DM: basal control with differentiated medium (2% Horse serum, 1% Penicillin Streptomycin, DMEM high glucose). TNFa 10 ng/ml: tumor necrosis factor alpha at a concentration of 1 Ong/ml in DM. OLP 1.5 μM: Oleuropein at a concentration of 1.5 μM in DM. TNFa 10 ng/ml+ OLP 1.5 μM: tumor necrosis factor alpha at a concentration of 10 ng/ml with Oleuropein at a concentration of 1.5 μM in DM FIG. 5 shows the effect of oleuropein (OLP) at 1.5 μM on Chemokine (C—C motif) ligand 5 (CCL-15) expression also known as RANTES (regulated on activation, normal T cell expressed and secreted). Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M. DM: basal control with differentiated medium (2% Horse serum, 1% Penicillin Streptomycin, DMEM high glucose). TNFa 10 ng/ml: tumor necrosis factor alpha at a concentration of 1 Ong/ml in DM. OLP 1.5 μM: Oleuropein at a concentration of 1.5 μM in DM. TNFa 10 ng/ml+ OLP 1.5 μM: tumor necrosis factor alpha at a concentration of 10 ng/ml with Oleuropein at a concentration of 1.5 μM in DM FIG. 6 shows the effect of oleuropein (OLP) at 1.5 μM on A disintegrin and metalloproteinase with thrombospondin motifs 4 (ADAMTS-4) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M.

DM: basal control with differentiated medium (2% Horse scrum, 1% Penicillin Streptomycin, DMEM high glucose). TNFa 10 ng/ml: tumor necrosis factor alpha at a concentration of 1 Ong/ml in DM. OLP 1.5 μM: Oleuropein at a concentration of 1.5 μM in DM. TNFa 10 ng/ml+ OLP 1.5 μM: tumor necrosis factor alpha at a concentration of 1 Ong/ml with Oleuropein at a concentration of 1.5 μM in DM.

Figure 7:
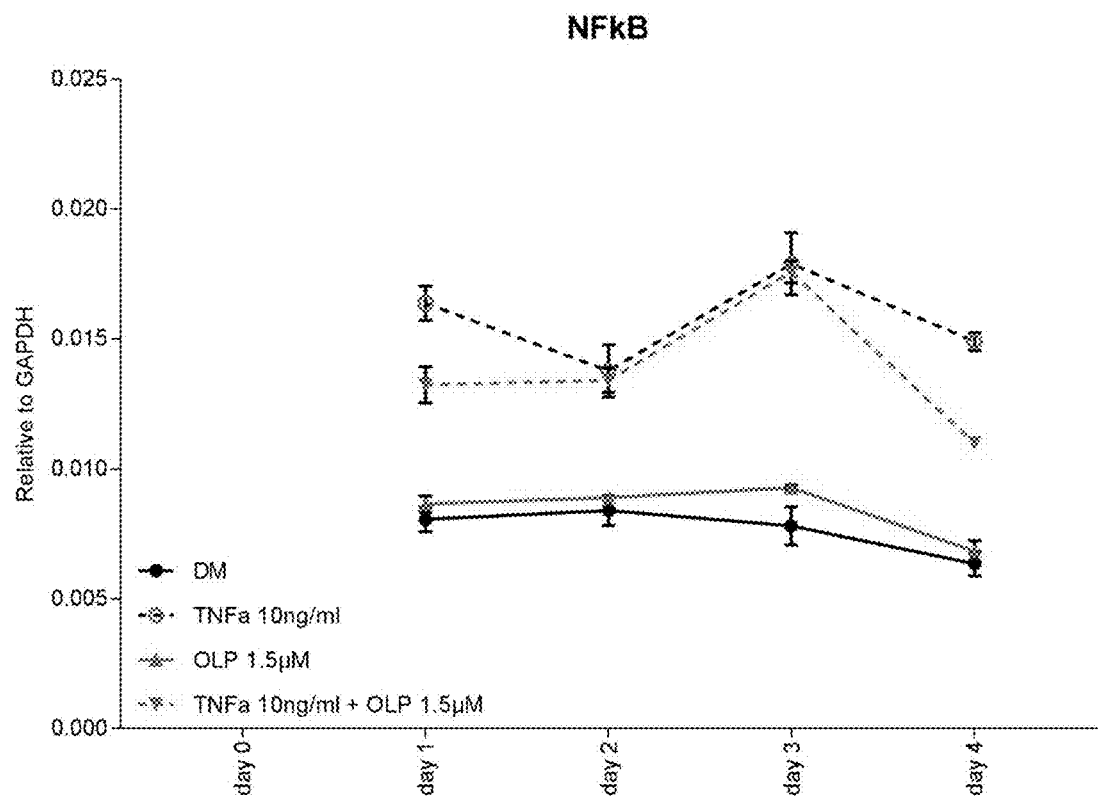

FIG. 7 shows the effect of oleuropein (OLP) at 1.5 μM on NF-κB (nuclear factor kappa-light-chain-enhancer of activated B cells) expression. Murine myoblasts (C2C 12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as meant S.E.M. DM: basal control with differentiated medium (2% Horse serum, 1% Penicillin Streptomycin, DMEM high glucose). TNFa 10 ng/ml: tumor necrosis factor alpha at a concentration of 10 ng/ml in DM. OLP 1.5 μM: Oleuropein at a concentration of 1.5 μM in DM. TNFa 10 ng/ml+ OLP 1.5 μM: tumor necrosis factor alpha at a concentration of 10 ng/ml with Oleuropein at a concentration of 1.5 μM in DM.

Figure 8:
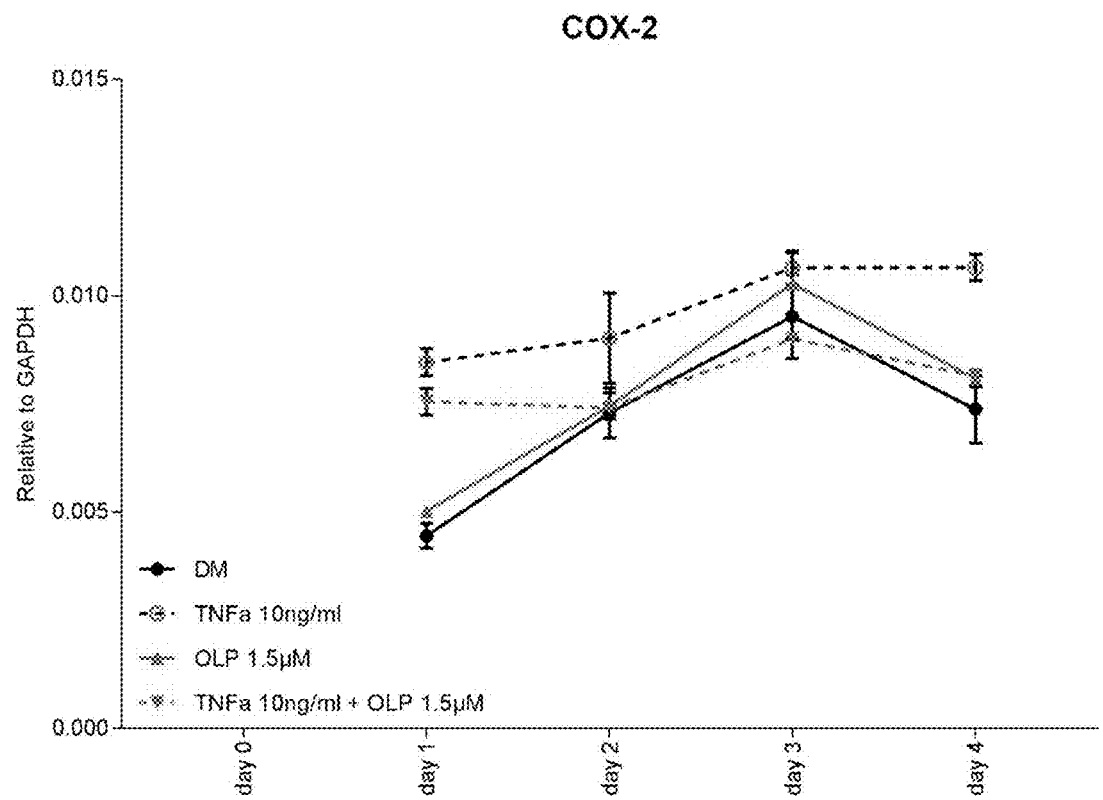

FIG. 8 shows the effect of oleuropein (OLP) at 1.5 μM on Prostaglandin-endoperoxide synthase 2 also known as cyclooxygenase-2 (COX-2) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M. DM: basal control with differentiated medium (2% Horse serum, 1% Penicillin Streptomycin, DMEM high glucose). TNFa 10 ng/ml: tumor necrosis factor alpha at a concentration of 10 ng/ml in DM. OLP 1.5 μM: Oleuropein at a concentration of 1.5 μM in DM. TNFa 10 ng/ml+ OLP 1.5 μM: tumor necrosis factor alpha at a concentration of 10 ng/ml with Oleuropein at a concentration of 1.5 μM in DM.

Figure 9:
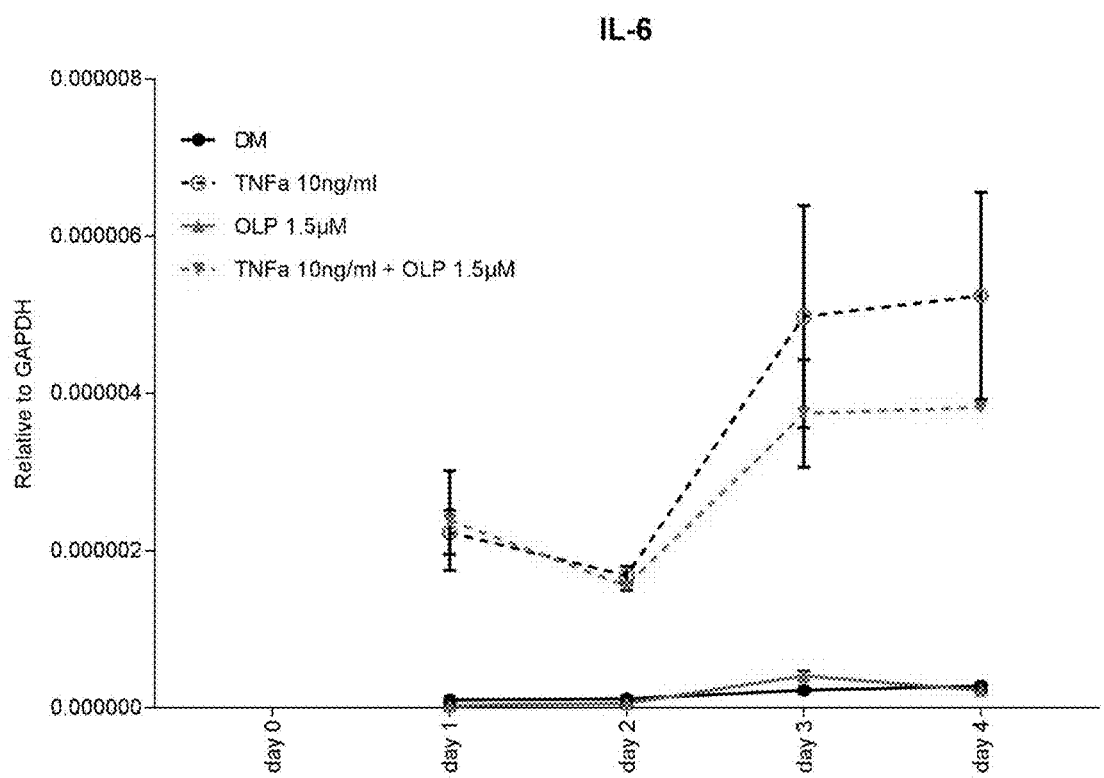
Figure 10:
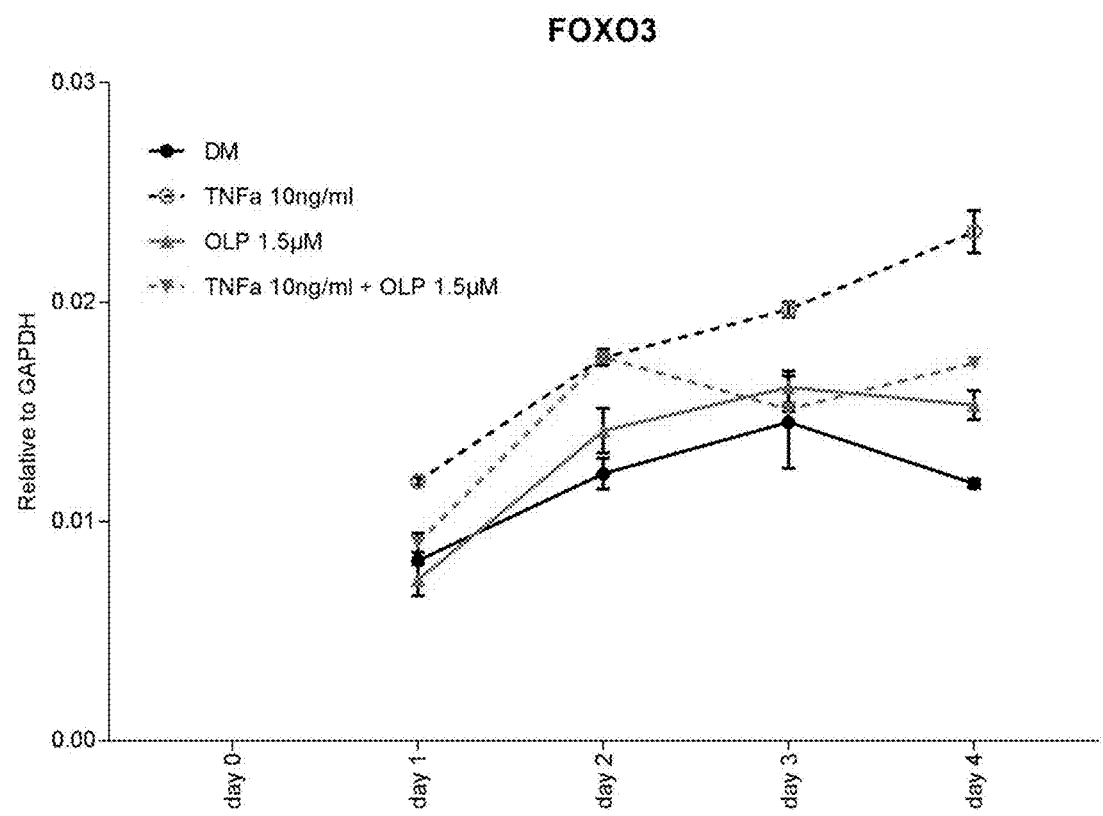

FIG. 9 shows the effect of oleuropein (OLP) at 1.5 μM on Interleukin-6 (IL-6) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean f S.E.M. DM: basal control with differentiated medium (2% Horse serum, 1% Penicillin Streptomycin, DMEM high glucose). TNFa 10 ng/ml: tumor necrosis factor alpha at a concentration of 10 ng/ml in DM. OLP 1.5 μM: Oleuropein at a concentration of 1.5 μM in DM. TNFa 10 ng/ml+ OLP 1.5 μM: tumor necrosis factor alpha at a concentration of long/ml with Oleuropein at a concentration of 1.5 μM in DM FIG. 10 shows the effect of oleuropein (OLP) at 1.5 μM on Forkhead box 03 (FOXO3) expression. Murine myoblasts (C2C12) were culture in monolayer during 4 days with or without oleuropein in presence or in absence of TNF-α stimulation (10 ng/ml). Data were normalized to GAPDH (Glyceraldehyde 3-phosphate dehydrogenase) mRNA levels and results were expressed as mean±S.E.M. DM: basal control with differentiated medium (2% Horse serum, 1% Penicillin Streptomycin, DMEM high glucose). TNFα 10 ng/ml: tumor necrosis factor alpha at a concentration of 10 ng/ml in DM. OLP 1.5 μM: Oleuropein at a concentration of 1.5 μM in DM. TNFa 10 ng/ml+ OLP 1.5 μM: tumor necrosis factor alpha at a concentration of 10 ng/ml with Oleuropein at a concentration of 1.5 μM in DM Taken together these results suggested that oleuropein counteract the effect of inflammation through inflammatory pathways to limit protein degradation and stimulate muscle hypertrophy.

Figure 11:
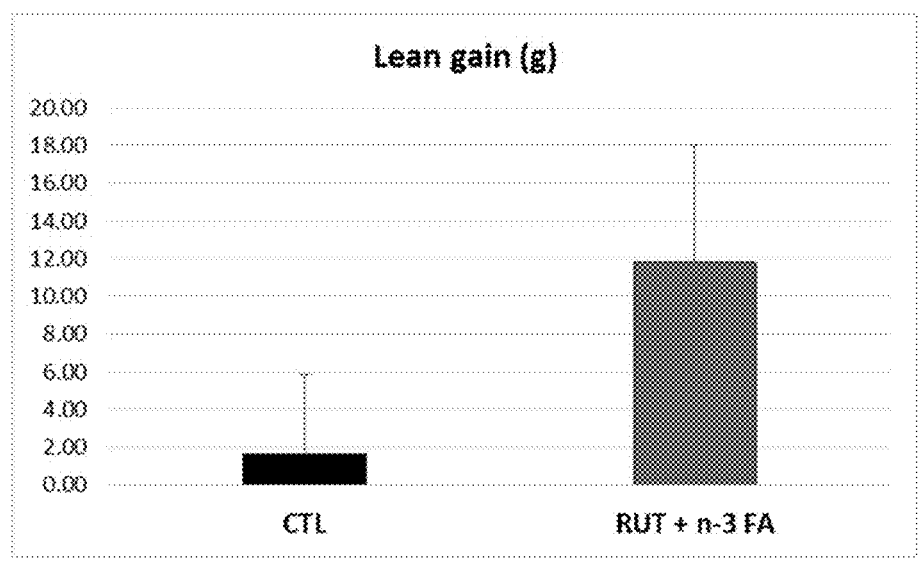

Exp. 3: Old rats are a good model to assess the effect of nutritional intervention in age related muscle decline. With this model, it can be observed as in human a decrease in muscle mass and function with age. In this model used by the present inventors, 20 months-old rats were fed either with a normal diet or with the same diet supplemented with one polyphenol, rutin, and n-3 fatty acid (n-3 FA) for 3 months. Lean gain measured by Nuclear Magnetic Resonance (NMR) was significantly higher in the rutin+n-3 FA group compared with the control group. The decline of gait speed observed with age, a parameter for mobility, was significantly reduced with rutin+n-3 FA supplementation. Low grade inflammation was evaluated by measuring alpha-2 macroglobulin circulating concentration and was decreased by rutin and n-3 FA. (FIG. 11-13) FIG. 11, shows the effect of rutin and n-3 fatty acids (RUT+n-3 FA) on lean gain in old rats. 20 months-old rats were fed either a control diet or the same diet supplemented with rutin and n-3 FA for 3 months. Results were expressed as mean±S.E.M. CTL: control diet. RUT+n-3 FA: control diet with rutin and n-3 fatty acids.

Figure 12:
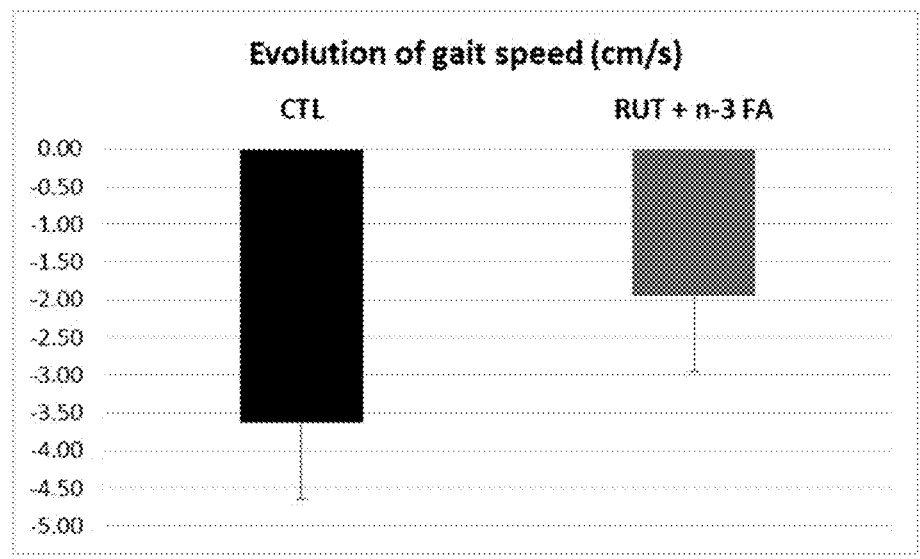

Then, FIG. 12 shows the effect of rutin and n-3 fatty acids (RUT+n-3 FA) on evolution of gait speed from baseline to 3 months supplementation in old rats. 20 months-old rats were fed either a control diet or the same diet supplemented with rutin and n-3 FA 18 for 3 months. Results were expressed as mean±S.E.M. CTL: control diet. RUT+n-3 FA: control diet with rutin and n-3 fatty acids.

Figure 13:
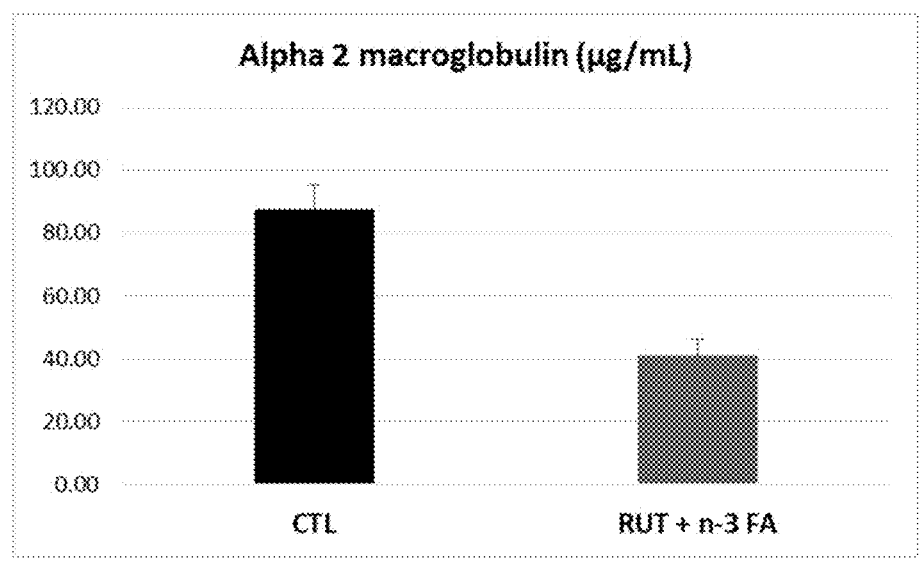

Also, FIG. 13 shows the effect of rutin and n-3 fatty acids (RUT+n-3 FA) on low grade inflammation (alpha 2 macroglobulin) in old rats. 20 months-old rats were fed either a control diet or the same diet supplemented with rutin and n-3 FA for 3 months. Results were expressed as mean±S.E.M. CTL: control diet. RUT+n-3 FA: control diet with rutin and n-3 fatty acids Taken together, these results suggested that rutin and n-3 FA supplementation reduced the loss of muscle mass and improved functionality in old rats. This was associated with a decrease of low grade inflammation.

Exp. 4: Models similar to Experiment 3 above were used. In this experiment, 20 months-old rats were fed either with a normal diet or with the same diet supplemented with curcumin, rutin or n-3 fatty acid (n-3 FA) alone or in combination. The decline of gait speed observed with age, a parameter for mobility, was significantly reduced with curcumin supplementation. It decreased only by 4% with curcumin versus −18% with control. It clearly shows that the effect is polyphenol specific since rutin did not bring any effect. On top of that the presence of n-3 FA induces even stronger effect with only 2% decrease of gait speed. MFN2/DRP1 protein level ratio, a marker of mitochondrial activity (fusion/fission) is going in the same direction with a significant increase with the combination of curcumin and n-3 FA. Mitochondrial respiratory complexes activities measured by colorimetry was synergistically enhanced in the curcumin and n-3 FA group, suggesting a better mitochondrial energy production. (FIG. 14-16).

Figure 14:
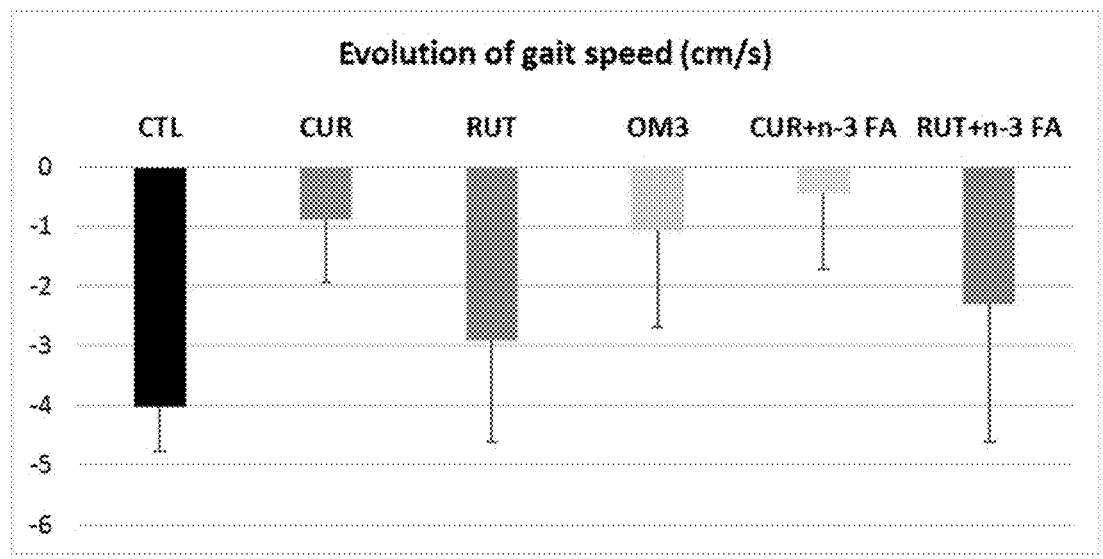

FIG. 14 shows the effect of curcumin (CUR), rutin (RUT), n-3 fatty acid (n-3 FA) and the combination of either curcumin and n-3 FA (CUR+n-3 FA) or rutin and n-3 FA (RUT+n-3 FA) on evolution of gait speed from baseline to 3 months supplementation in old rats. 20 months-old rats were fed either a control diet or the same diet supplemented with polyphenols and n-3 fatty acid alone or in combination for 3 months. Results were expressed as mean±S.E.M. CTL: control diet. CUR: control diet with curcumin. RUT: control diet with rutin. n-3 FA: control diet with n-3 fatty acid. CUR+n-3 FA: control diet with curcumin and n-3 fatty acids. RUT+n-3 FA: control diet with rutin and n-3 fatty acids.

Figure 15:
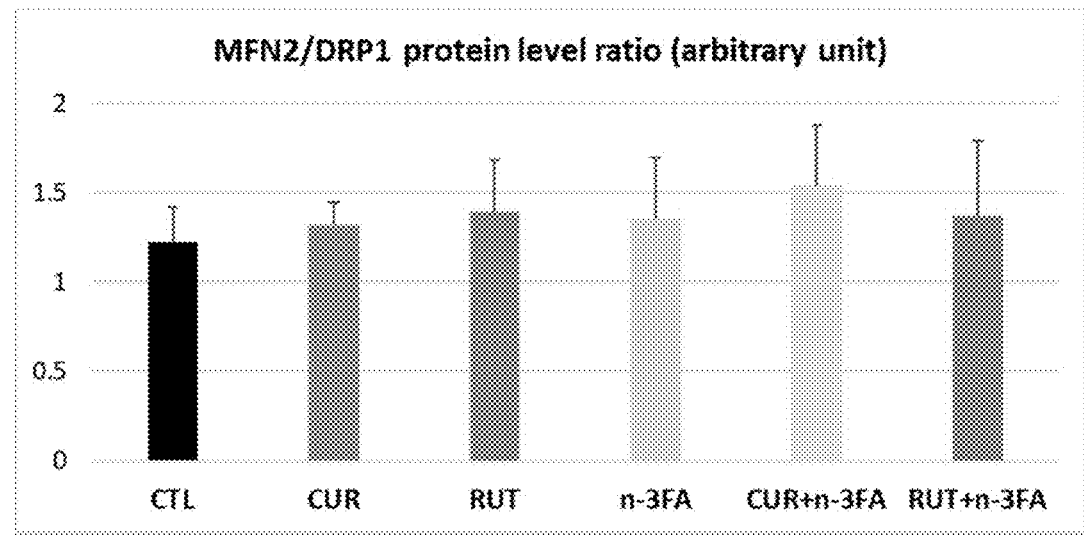

Then, FIG. 15 shows the effect of curcumin (CUR), rutin (RUT), n-3 fatty acid (n-3 FA) and the combination of either curcumin and n-3 FA (CUR+n-3 FA) or rutin and n-3 FA (RUT+n-3 FA) on MFN2 protein level in old rats. 20 months-old rats were fed either a control diet or the same diet supplemented with polyphenols and n-3 fatty acid alone or in combination. Results were expressed as mean±S.E.M. CTL: control diet. CUR: control diet with curcumin. RUT: control diet with rutin. n-3 FA: control diet with n-3 fatty acid. CUR+n-3 FA: control diet with curcumin and n-3 fatty acids. RUT+n-3 FA: control diet with rutin and n-3 fatty acids.

Figure 16:
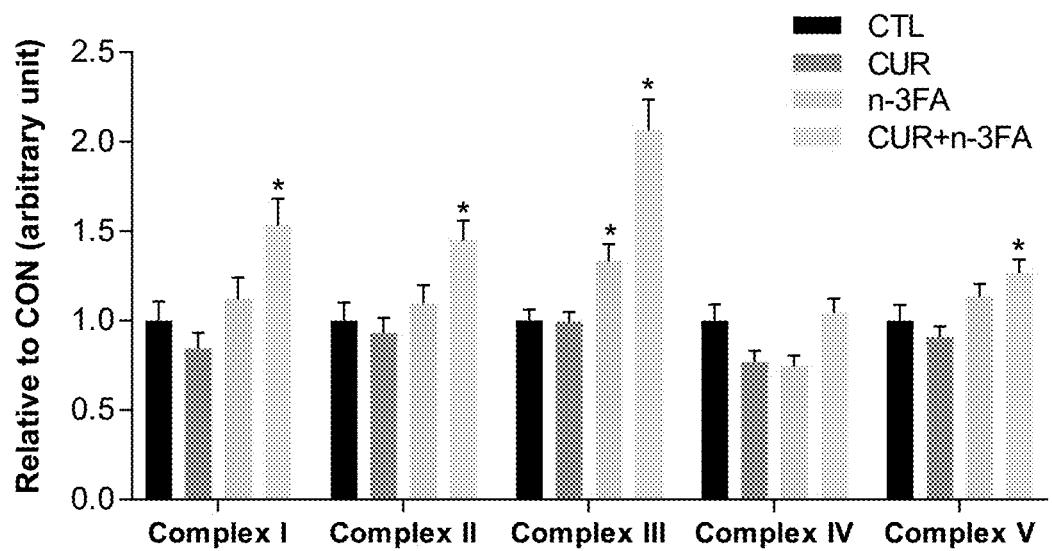
FIG. 16: Effect of curcumin (CUR), n-3 fatty acid (n-3 FA) and the combination of curcumin and n-3 FA (CUR+n-3 FA) on mitochondrial complexes activity in old rats. 20 months-old rats were fed either a control diet or the diet supplemented with curcumin and optionally n-3 FA. Results were expressed as mean±S.E.M.

Finally, FIG. 16 shows the effect of curcumin (CUR), n-3 fatty acid (n-3 FA) and the combination of both (CUR+n-3 FA) on mitochondrial complexes activity in old rats. 20 months-old rats were fed either a control diet or the same diet supplemented with polyphenols and n-3 fatty acid alone or in combination. Results were expressed as mean±S.E.M. CTL: control diet. CUR: control diet with curcumin. n-3 FA: control diet with n-3 fatty acid. CUR+n-3 FA: control diet with curcumin and n-3 fatty acids.

Taken together, these results suggested that curcumin supplementation had superior effect on muscle functionality in old rats. This was associated with an improvement of mitochondrial function. The presence of n-3 FA with curcumin induced even a stronger effect.

The invention is claimed as follows:

1. A method of reducing a loss of muscle functionality in an individual, increasing muscle functionality in an individual, and/or improving recovery of muscle functionality after muscle atrophy in an individual, the method consisting essentially of administering an effective amount of a combination of curcumin and omega-3 fatty acid to the individual.

2. The method of claim 1, wherein the muscle functionality comprises a characteristic selected from the group consisting of muscle strength, gait speed, and combinations thereof.

3. The method of claim 1, wherein the muscle functionality comprises gait speed.

4. The method of claim 1, wherein the individual has sarcopenia or is an elderly having mobility issues or muscle weakness.

5. A method of reducing a loss of gait speed in an individual, increasing gait speed in an individual, and/or improving recovery of gait speed after muscle atrophy in an individual, the method consisting essentially of administering an effective amount of a combination of curcumin and omega-3 fatty acid to the individual.

6. A method of treating, reducing an incidence of, reducing a severity of, and/or preventing sarcopenia, the method consisting essentially of administering an effective amount of a combination of curcumin and omega-3 fatty acid to an individual.

7. The method of claim 5, wherein the individual has sarcopenia or is an elderly having mobility issues or muscle weakness.

8. The method of claim 6, wherein the individual has sarcopenia or is an elderly having mobility issues or muscle weakness.

* * * * *